(12) United States Patent
Im et al.

(10) Patent No.: US 7,285,120 B2
(45) Date of Patent: Oct. 23, 2007

(54) BALLOON CENTERED RADIALLY EXPANDING ABLATION DEVICE

(75) Inventors: Karl S. Im, San Jose, CA (US); John T. To, Newark, CA (US); Roger W. Perkins, Sunnyvale, CA (US)

(73) Assignee: Venture Manufacturing, LLC, Santa Clara, CA (US)

( * ) Notice: Subject to any disclaimer, the term of this patent is extended or adjusted under 35 U.S.C. 154(b) by 68 days.

(21) Appl. No.: 10/855,656

(22) Filed: May 27, 2004

(65) Prior Publication Data

US 2004/0243124 A1 Dec. 2, 2004

Related U.S. Application Data

(60) Provisional application No. 60/473,774, filed on May 27, 2003.

(51) Int. Cl.
*A61B 18/18* (2006.01)
(52) U.S. Cl. .......................... 606/41; 607/122
(58) Field of Classification Search ................ 606/41, 606/49, 50; 607/96, 101, 113, 116, 102, 607/122
See application file for complete search history.

(56) References Cited

U.S. PATENT DOCUMENTS

| | | | |
|---|---|---|---|
| 5,366,490 A | 11/1994 | Edwards et al. | |
| 5,471,982 A * | 12/1995 | Edwards et al. | 600/374 |
| 5,800,378 A * | 9/1998 | Edwards et al. | 604/22 |
| 6,106,460 A * | 8/2000 | Panescu et al. | 600/300 |
| 6,454,758 B1 | 9/2002 | Thompson et al. | |
| 6,595,989 B1 | 7/2003 | Schaer | |
| 6,607,502 B1 | 8/2003 | Maguire et al. | |
| 6,668,198 B2 | 12/2003 | Swanson et al. | |
| 6,997,925 B2 * | 2/2006 | Maguire et al. | 606/41 |
| 2002/0133150 A1 | 9/2002 | Whayne et al. | |
| 2002/0151888 A1 * | 10/2002 | Edwards et al. | 606/41 |
| 2003/0083653 A1 | 5/2003 | Maguire et al. | |
| 2003/0111085 A1 | 6/2003 | Lesh | |
| 2003/0144658 A1 | 7/2003 | Schwartz et al. | |
| 2003/0191463 A1 | 10/2003 | Stewart et al. | |
| 2003/0195506 A1 | 10/2003 | Stewart et al. | |
| 2003/0195507 A1 | 10/2003 | Stewart et al. | |
| 2003/0195510 A1 | 10/2003 | Schaer | |
| 2003/0204186 A1 | 10/2003 | Geistert | |
| 2003/0204187 A1 | 10/2003 | Hintringer et al. | |
| 2004/0019349 A1 | 1/2004 | Fuimaono et al. | |
| 2004/0034347 A1 | 2/2004 | Hall et al. | |
| 2004/0049181 A1 | 3/2004 | Stewart et al. | |
| 2004/0054360 A1 | 3/2004 | Schwartz et al. | |
| 2004/0054367 A1 | 3/2004 | Jimenez, Jr. et al. | |
| 2004/0082948 A1 | 4/2004 | Stewart et al. | |

* cited by examiner

*Primary Examiner*—Michael Peffley
(74) *Attorney, Agent, or Firm*—Morrison & Foerster LLP

(57) ABSTRACT

A device and associated method for performing ablation procedures on anatomical structures accessible from within the chambers of the heart to form lesions that electrically isolate the tissue.

8 Claims, 4 Drawing Sheets

BALLOON CENTERED RADIALLY EXPANDING ABLATION DEVICE

This application claims the benefit and priority of U.S. Provisional Patent Application Ser. No. 60/473,774, filed May 27, 2003, which is herein incorporated by reference for all purposes.

BACKGROUND

1. Field of the Invention

The invention generally relates to the treatment of electrophysiological disease, and more particularly to devices and methods for ablating tissue in treating atrial fibrillation.

2. Related Art

A procedure known as the surgical maze procedure has been developed for treating atrial fibrillation, a condition which results from, disorganized electrical activity in the heart muscle or myocardium. The surgical maze procedure involves the creation of a series of surgical incisions in a preselected pattern so as to create conductive corridors of viable tissue bounded by scar tissue.

Ablative procedures have been used as an alternative to the surgical incisions used in the maze procedure. Typically, the ablative techniques include endocardial or epicardial ablation, which create lesions extending through a sufficient thickness of the myocardium to block electrical conduction.

Unfortunately, the maze procedure, whether using surgical or ablative techniques, is often very time-consuming and can result in lesions which do not completely encircle the pulmonary veins or which contain gaps and discontinuities. Most procedures do not include means for visualization of endocardial anatomy and most endovascular devices are often inadequate in relaying the precise position of such devices in the heart. This may result in misplaced lesions.

SUMMARY

The present invention provides a device and associated method for performing ablation procedures on anatomical structures accessible from within the chambers of the heart to form lesions that electrically isolate the tissue.

The method includes placing at least one ablation device through the major vein or artery usually in the neck or groin area, and guided into the heart chambers; deploying an inflatable balloon at an orifice within the cardiac myocardium in which the balloon can be anchored; radially deploying at least one ablation element; and ablating the heart wall with at least one ablation element to create at least one lesion.

In another aspect of the invention, an apparatus for forming a lesion in the heart wall includes an ablation device including a catheter body concentrically formed with an outer sheath having a distal end and a proximal end; a balloon coupled at the distal end to perform a centering and anchoring function at an orifice within the cardiac myocardium; at least one ablation element positioned proximal to the balloon which can be radially deployed with respect to the central axis of the apparatus for creating a lesion in the heart wall. The apparatus may also include a control device at the proximal end for manipulating the ablation device.

The ablation element may be a radiofrequency electrode, microwave transmitter, cryogenic element, laser, ultrasonic transducer or any of the other known types of ablation devices suitable for forming lesions. The apparatus includes a plurality of such ablation devices arranged along the working end in a linear pattern suitable for forming a continuous, uninterrupted lesion around the orifice of heart vasculature or around the ostium of the pulmonary veins.

These and other features and advantages of the present invention will be more readily apparent from the detailed description of the preferred embodiments set forth below taken in conjunction with the accompanying drawings.

DETAILED DESCRIPTION

Figure 1A:
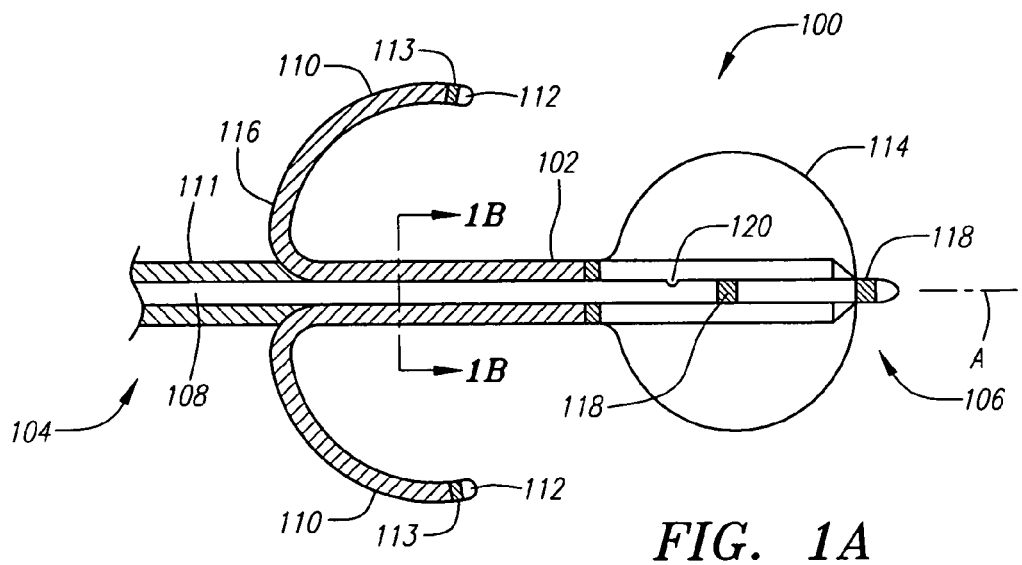
FIG. 1A is a simplified side view of an ablation device in accordance with an embodiment of the present invention.
Figure 1B:
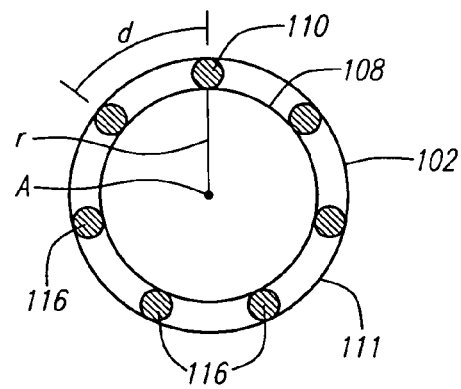
FIG. 1B is a simplified sectional view as indicated of a cross section of the embodiment of FIG. 1A.
Figure 1C:
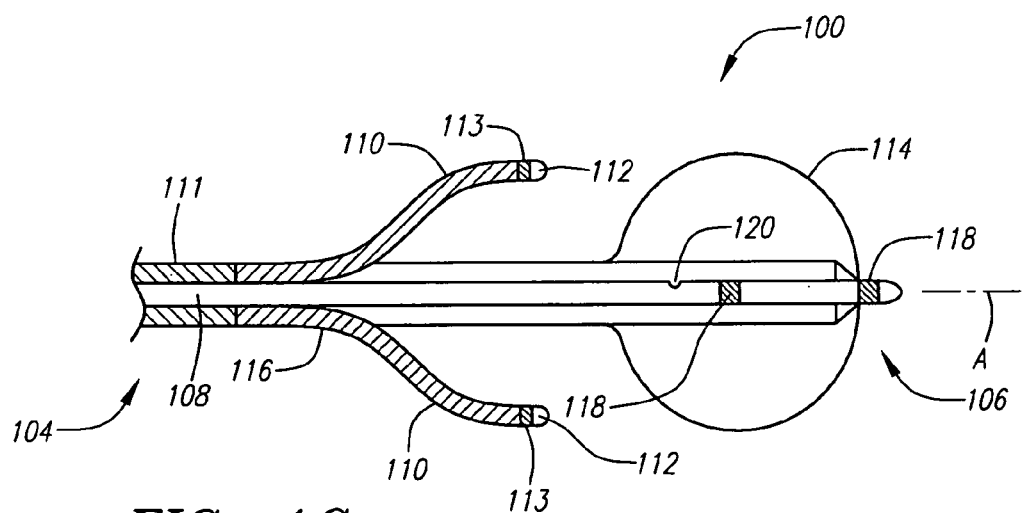
FIG. 1C is a simplified side view of an ablation device shown with alternate ablating member within the sheath in accordance with an embodiment of the present invention.

FIG. 1A and FIG. 1C are simplified side cross-sectional views of an embodiment of ablation device 100 in accordance with the present invention. In this embodiment, ablation device 100 includes a catheter body 102 having a proximal end 104 and a distal end 106 with a balloon 114 formed at distal end 106. Catheter body 102 includes an inflation/deflation lumen 108 surrounded by an outer sheath 111 formed concentric with lumen 108. In one embodiment, outer sheath 111 can be made to translate over lumen 108 in a telescopic arrangement.

Catheter body 102 and balloon 114 of ablation device 100 are configured for insertion into a main vein or artery through a small percutaneous incision. The extreme proximal end of ablation device 100 is operably coupled to a control device (not shown) used for manipulating ablation device 100 from outside the vein or artery. In one embodiment, ablation device 100 is made to enter the left heart chamber and advanced to the pulmonary veins. Ablation device 100 is made flexible enough to allow advancement to the heart chambers and can be made to any suitable dimension to reach the desired location within the heart chamber. Ablation device 100 can be made of a flexible biocompatible polymer or polymer matrix with metal wire braids and can include radiopaque markers 118 or radiopaque filler such as bismuth or barium sulfate.

FIG. 1B is a sectional view as indicated of a cross section of catheter body 102 of FIG. 1A. As shown in FIG. 1B, outer sheath 111 can include one to a plurality of smaller element housing lumens 116 configured to receive an ablation element 110. The one to a plurality of ablation elements 110 are used to form lesions isolating the pulmonary veins from the surrounding myocardium.

In one embodiment, each ablation element 110 disposed in lumens 116 includes a pre-shaped wire. In one embodiment, ablation elements 110 may include an energy tip 112 formed at the most distal end of the element. As described in detail below, energy tip 110 may include, for example, an RF electrode or other type of energy source capable of performing ablation of tissue. Thermocouples 113 can also be positioned proximate to energy tip 112, or may be welded or bonded to the energy tips themselves, to monitor the amount of heat generated at the ablation site and to facilitate temperature measurement of the target tissue during ablation and thus, prevent overheating. Thermocouples 113 can be coupled to wires which extend to proximal end 104 of ablation device 100 and ultimately to temperature monitoring equipment or electrical monitoring equipment as to facilitate mapping of electrical activity at the target sites.

Figure 2:
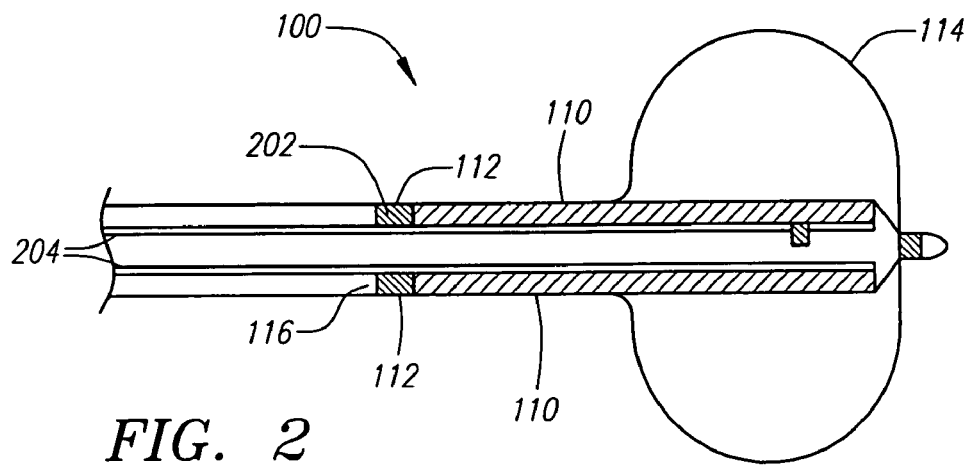
FIG. 2 is a side cross sectional view of yet another embodiment of the present invention.

As shown in FIG. 2, the pre-shaped wire can be received within lumens 116 and aligned parallel to a central axis A of catheter body 102. Openings 202 are formed along outer sheath 111 to allow ablation elements 110 to exit from lumen 116. In one embodiment, ablation elements 110 exit lumens 116 in a direction toward proximal end 104 through openings 202 while in one embodiment, ablation elements 110 can be made to exit lumens 116 in direction toward distal end 106 as shown in FIG. 1C. As the ablation elements 110 exit lumens 116 the pre-shaped wires radially expand away from central axis A, while at the same time the pre-shaped wire begins to regain its arcuate shape causing energy tip 112 to translate toward distal 106 (FIG. 1A). Generally, as described in greater detail below, the bend in arcuate shaped ablation element 110 causes energy tip 112 to advance toward the ablation site.

Ablation elements 110 include electrodes 112 formed at the distal end of ablation elements 110 for delivering current to the myocardium so as to create lesions of sufficient depth to block electrical conduction. Electrodes 112 may be solid metal rings or cylinders, foil strips, wire coils or other suitable construction for producing elongated lesions. It is understood that the term electrodes 112 as used herein may refer to any suitable ablating element 112, such as microwave transmitters, cryogenic elements, lasers, heated elements, ultrasound, hot fluid or other types of ablation devices suitable for forming lesions.

Referring again to FIG. 1B, ablation elements 110 are disposed in outer sheath 111 spaced apart a distance d about the circumference of sheath 111. The number of ablation elements 110 disposed in outer sheath 111 is variable and depends on the desired procedure. In one embodiment, each ablation element 110 is positioned a distance r from the central axis A. In one embodiment, ablation elements 110 are positioned so as to facilitate lesion formation on the three-dimensional topography of the myocardium. Ablation elements 110 can be made of any flexibly resilient material that possess a spring quality and can be pre-shaped, such as Nitinol and other memory shape metals, stainless steel, and steel alloys, and the like.

Proximal end 104 of ablation device 100 further includes a control handle (not shown) which locates distal end 106 at one of the pulmonary veins. The control end includes a handle and one to a plurality of slidable actuators, which are used to extend each ablation element 110 from lumens 116. An electrical connector suitable for connection to an energy source can be mounted to the handle.

As shown in FIG. 2, electrical wires, disposed in electric conduits 204, can be used to electrically couple the energy source to ablation elements 110 and ultimately electrodes 112. Each electrode 112 can be coupled to a separate wire to allow any electrode 112 or combination of electrodes to be selectively activated. The thermocouples mounted near the electrodes can be coupled to temperature or electrical monitoring equipment to control temperature of selected electrode 112 and monitor electrical activity at the target site. Also mounted to the handle can be a connector for connection to a source of inflation fluid or suction, used for the inflation/deflation of balloon 114.

In one embodiment, the actuators in the handle are coupled to the proximal end of each ablation element 110, and may be advanced forward to deploy each ablation element 110 from a non-deployed or retracted orientation, as shown in FIG. 2 to a deployed or radially expanded orientation, as shown in FIG. 1A.

The ablating element captured within the outer sheath 111 is free to transverse and rotate relative to the inner lumen 108. This allows the positioning of the radially expanded ablating element and its electrode 112 to vary in distance relative to the location of the anchoring balloon 114 and rotate along the central axis of the anchored balloon 114. Alternatively, outer sheath 111 and inner lumen 108 are coupled in a slidable relationship while the ablating element is captured in between the outer sheath 111 and inner lumen 108 and not part of the outer sheath 111. In this alternative embodiment, outer sheath 111 can be pulled back relative to inner lumen 108 which causes ablation elements to become exposed, which allows ablation elements to radially expand due to their shaped memory and be directed to the tissues to be ablated.

Figure 3A:
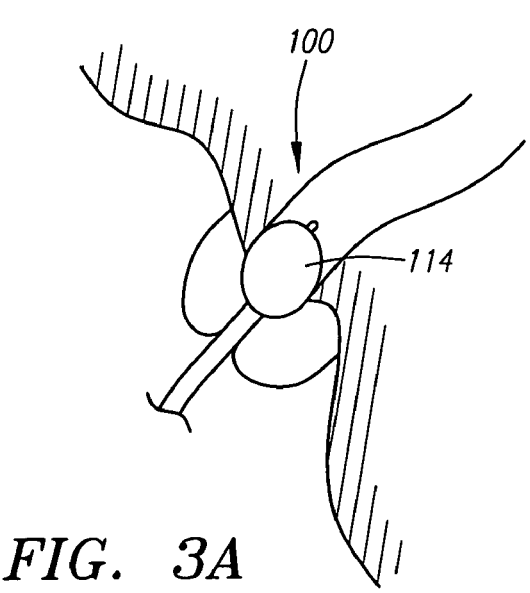
FIGS. 3A and 3B are simplified illustrations of a deployed ablation device in accordance with an embodiment of the present invention.
Figure 3B:
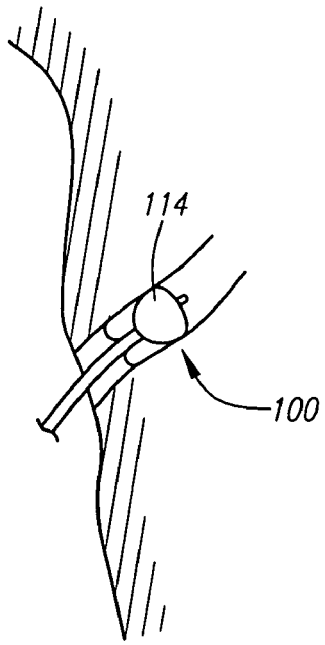

Referring again to FIGS. 1A and 2, balloon 114 is positioned at the distal end 106 of ablation device 100 just distal to ablation elements 110. Balloon 114 is used to position and manipulate ablation elements 110. In operation, inner lumen 108 is configured to carry a gas or fluid through opening 120, to or away from balloon 114, to cause the balloon to inflate or deflate as desired. As shown in FIGS. 3A and 3B, the size of the inflated balloon 114 controls the range of the ablation site along the axis of the vasculature. For example, balloon 114 can be used to anchor ablation device 100 at the opening of the vasculature (FIG. 3A). Alternatively, ablation device 100 can be allowed to enter into the vasculature and expanded to anchor ablation device 100 upstream of the vascular opening. In any embodiment, the inflated balloon is used to position and manipulate the ablation element 110.

FIG. 1C is a simplified illustration of an alternative embodiment of ablation device 100. In this alternative embodiment, ablation elements 110 are deployed forward toward distal end 106. Upon exiting outer sheath 111, ablation elements 110 take a pre-shaped form which causes them to bend around balloon 114 and avoid contact therewith.

Figure 4:
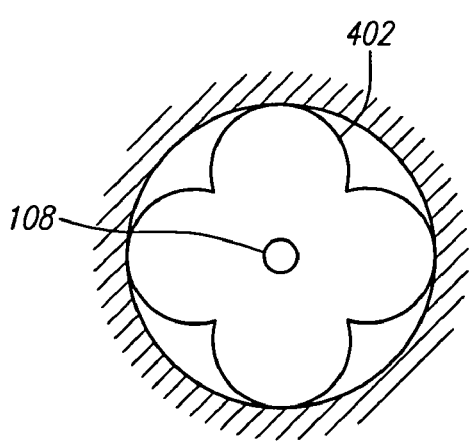
FIG. 4 is a simplified cross sectional view of a balloon in accordance with an embodiment of the present invention.

As shown in FIG. 4, in one embodiment, balloon 402 is formed of multi-chambers in a shape other than a sphere. Inner lumen 108 can include multiple openings 120, to feed gas or liquid into each chamber of balloon 402. For example, balloon 402 can be made with a clove-like shape. The clover like shaped balloon can anchor ablation device 100 within an orifice at the highest points of the clover-like shape, while allowing blood to flow between the recessed spaces formed between the multi-chamber sections.

In situations where the ostium is not normal to the axis of the vascular opening, ablation element 110 can be manipulated to contact the high and low points of the ostium by the use of balloon 114 having multi-chambers and independently controlled inflation chambers. For example, filling one of the chambers more or less against the other chambers can be used to bias ablation elements 110 to only contact specific quadrants of the circumferential pattern. Alternatively, the biasing of the elements to specific areas can be accomplished using a single chamber balloon and independent and selectively deploying the abating element. This may be controlled by the user at the handle.

The radially expanding ablation elements 110 can be made flexible enough to account for the varying topography of the opening.

Figure 5:
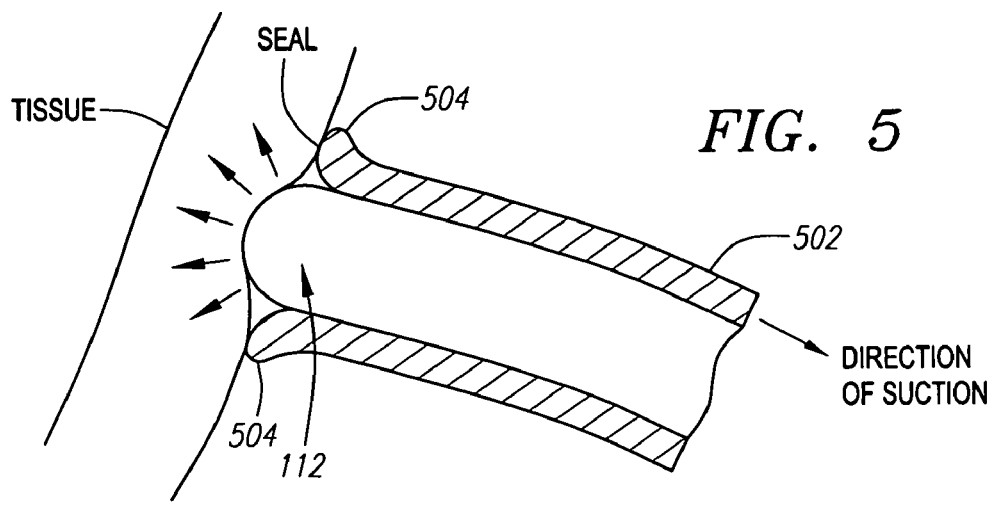
FIG. 5 is a simplified view of an ablation element including protective sheath in accordance with an embodiment of the present invention.

FIG. 5 is a simplified illustration of ablation element 110 including a protective sheath 502 which provides a more efficient energy delivery. Protective sheath 502 can be a non-conductive compliant polymer. The differential stiffness between the ablation element 110 and the protective sheath 502 pushes back the sheath relative to the tip of the ablation element to form an expanded lip portion or petal 504. Petal 504 provides increased impedance and provides minimal heating of blood surrounding electrode 112.

Protective sheath 502 can be made to seal against the tissue wall before electrode 112 is energized to minimize the contact with blood and to maximize the contact with the tissue. A soft suction within the sheath 502 can be used to cause the sheath 502 to seal against the soft tissue.

Figure 6:
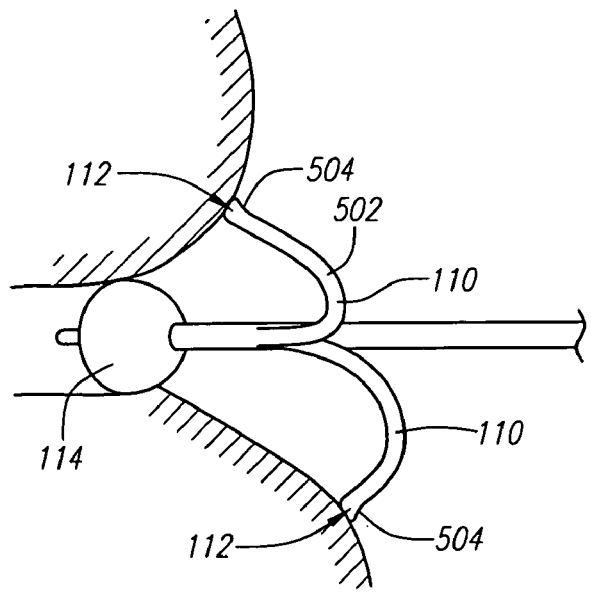
FIG. 6 is a simplified view of a deployed ablation device in accordance with an embodiment of the present invention.

As shown in FIG. 6, petal 504 at the end of sheath 502 can also provide a self-aligning footing for the un-even contours of the tissue wall by directing electrode 112 of ablation element 110 to contact the tissue perpendicular to the surface of the tissue. The flexible ablation element 110 can adjust to align the petal 504 perpendicular to the contact surface, since petal 504 will naturally try to bias ablation element 110 into such an orientation.

Ablation elements 110 can accomplish focal, segmented, or circumferential ablation concentric to balloon 114, which is deployed in an orifice of the vasculature, such as the pulmonary vein near its ostium.

In one embodiment, outer sheath 111 which houses ablation elements 110 is free to rotate with respect to inner lumen 108. Where a circumferential pattern is desired, the radially expanding ablation elements 110 can be indexed while the inner lumen 108 coupled to balloon 114 is anchored and remains stationary to complete the ablation concentric with a central axis of balloon 114.

Figure 8:
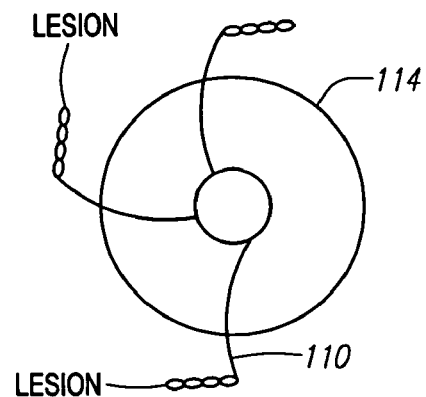
FIG. 8 is a simplified illustration of an embodiment of the present invention.
Figure 9A:
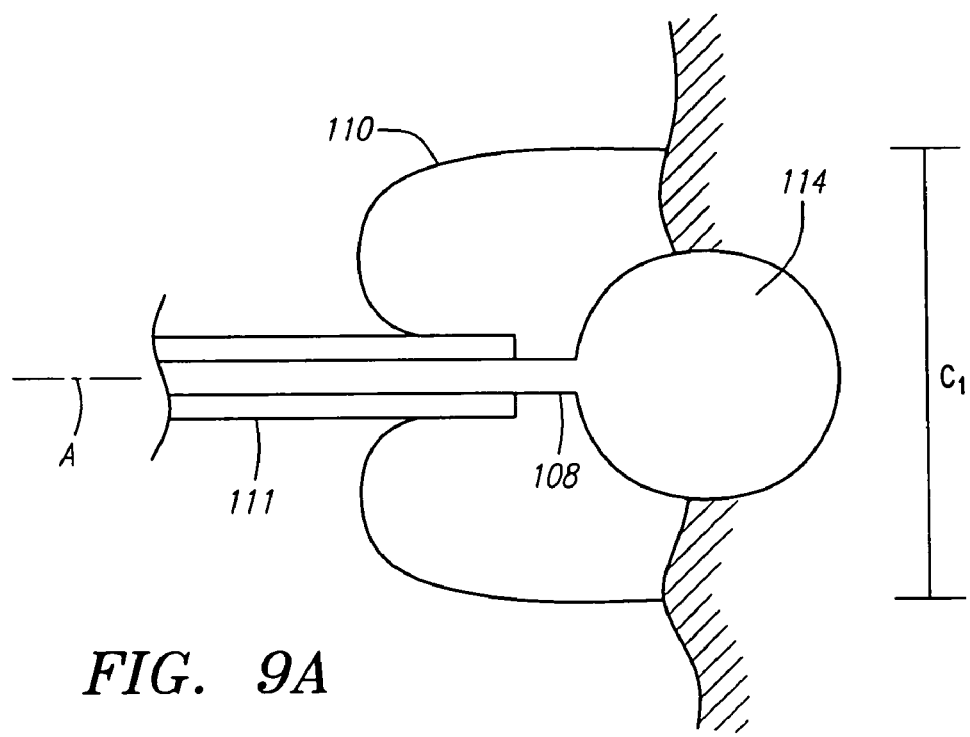
FIGS. 9A and 9B are a simplified illustration of an embodiment of the present invention.
Figure 9B:
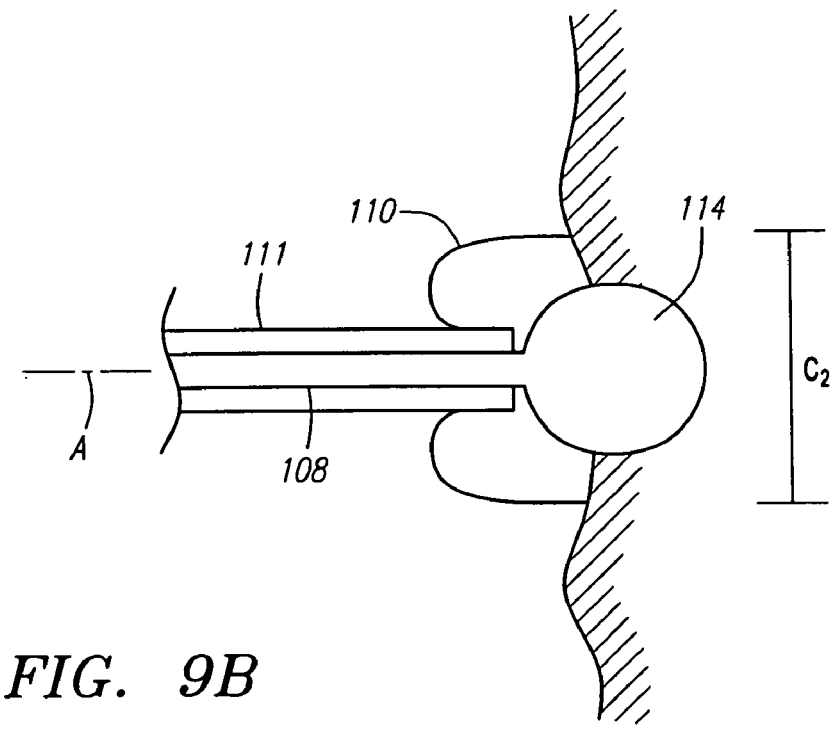

FIGS. 9A and 9B show that outer sheath 111 can be made to traverse along the central axis A to provide flexible positioning of ablation elements 110. The traversed position as well as the amount of radial deployment of ablation element 110 determines the size of the circumferential pattern and the precise location of the segmented focal lesion site (FIG. 8). For example, outer sheath 111 can be positioned such that ablation elements 110 deploy to form a circumferential pattern $C_1$ or positioned closer to balloon 114 to form circumferential pattern $C_2$.

Figure 7:
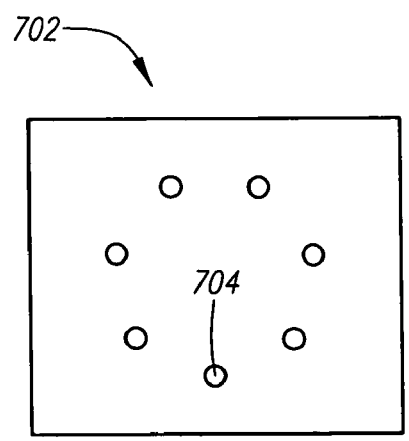
FIG. 7 is a simplified illustration of a display coupleable to the ablation device for showing the radially deployed ablation elements in accordance with an embodiment of the present invention.

FIG. 7 is a simplified illustration of a display feature 702 to show when contact has been made between ablation element 110 and the tissue. A visual display can be used with energy delivery equipment to show when optimum contact has been achieved (impedance). Display 702 shows a location of each radially deployed ablation element 110 that has made good contact with the target tissue.

In one embodiment, the LEDs 704 light up a pattern that corresponds to the contact points of the ablation elements 110 on the target tissue based on an impedance measurement at each electrode 112. Sensitivity setting can be adjusted to show whether the contact made is optimal or not or how close to optimal the contact has become.

Having thus described embodiments of the present invention, persons skilled in the art will recognize that changes may be made in form and detail without departing from the spirit and scope of the invention. Thus the invention is limited only by the following claims.

What is claimed is:

1. An apparatus for forming a lesion in the heart wall comprising:
    an ablation device including a catheter body concentrically formed with an outer sheath having a distal end and a proximal end;
    a balloon coupled at the distal end to perform a centering and anchoring function at an orifice within the cardiac myocardium;
    at least one pre-shaped ablation element positioned proximal to the balloon which can be radially deployed with respect to the central axis of the apparatus for creating a lesion at a lesion creation site in the heart wall; and
    a visual display feature integrated with energy source equipment configured to indicate evidence of contact made between the at least one ablation element and the lesion creation site;
    wherein said visual display feature comprises an LED pattern corresponding to a contact point between the at least one ablation element and the lesion creation site.

2. An apparatus for forming a lesion in the heart wall comprising:
    an ablation device including a catheter body concentrically formed with an outer sheath having a distal end and a proximal end;
    a balloon coupled at the distal end to perform a centering and anchoring function at an orifice within the cardiac myocardium;
    at least one pre-shaped ablation element positioned proximal to the balloon which can be radially deployed with respect to the central axis of the apparatus for creating a lesion at a lesion creation site in the heart wall; and
    a visual display feature integrated with energy source equipment configured to indicate evidence of contact made between the at least one ablation element and the lesion creation site;
    wherein said visual display feature comprises an adjustable sensitivity setting to indicate a level of contact between the at least one ablation element and the lesion creation site.

3. An apparatus for forming a lesion in the heart wall comprising:
    an ablation device including a catheter body concentrically formed with an outer sheath and inner lumen having a distal end and a proximal end;
    a balloon coupled at the distal end of the inner lumen to position the catheter;
    at least one ablation element positioned proximal to the balloon which can be radially deployed with respect to central axis of the apparatus and can be indexed while inner lumen remains stationary and can traverse along the central axis; and
    a visual display feature integrated with energy source equipment configured to indicate evidence of contact made between the at least one ablation element and the lesion creation site;
    wherein said visual display feature comprises an LED pattern corresponding to a contact point between the at least one ablation element and the lesion creation site.

4. An apparatus for forming a lesion in the heart wall comprising:
- an ablation device including a catheter body concentrically formed with an outer sheath and inner lumen having a distal end and a proximal end;
- a balloon coupled at the distal end of the inner lumen to position the catheter;
- at least one ablation element positioned proximal to the balloon which can be radially deployed with respect to central axis of the apparatus and can be indexed while inner lumen remains stationary and can traverse along the central axis; and
- a visual display feature integrated with energy source equipment configured to indicate evidence of contact made between the at least one ablation element and the lesion creation site;
- wherein said visual display feature comprises an adjustable sensitivity setting to indicate a level of contact between the at least one ablation element and the lesion creation site.

5. A method for creating a lesion in the heart wall to create an ablation pattern to electrically isolate the vasculature from the chamber and to create a segmental electrical isolation for treatment of cardiac arrhythmia, the method comprising:
- positioning at least one ablation catheter having proximal and distal portion into the heart chamber near a vasculature ostium, wherein the catheter comprises an outer sheath;
- deploying an inflatable balloon to position at least one expandable ablation element proximal to the balloon;
- traversing the outer sheath along the catheter body to expose the at least one ablation element in a radial direction relative to a central axis of the ablation catheter;
- advancing the exposed ablation element along an inner lumen of the catheter to cause said at least one ablation element to contact a chamber wall about the vasculature ostium; and
- ablating a lesion pattern on said chamber wall to electrically isolate the vasculature ostium;
- wherein said advancing the exposed ablation element comprises controlling the lesion pattern shape and size by allowing only a predetermined portion of the at least one ablation element to be exposed and to regain a preselected shape.

6. A method for creating a lesion in the heart wall to create an ablation pattern to electrically isolate the vasculature from the chamber and to create a segmental electrical isolation for treatment of cardiac arrhythmia, the method comprising:
- positioning at least one ablation catheter having proximal and distal portion into the heart chamber near a vasculature ostium, wherein the catheter comprises an outer sheath;
- deploying an inflatable balloon to position at least one expandable ablation element proximal to the balloon;
- traversing the outer sheath along the catheter body to expose the at least one ablation element in a radial direction relative to a central axis of the ablation catheter;
- advancing the exposed ablation element along an inner lumen of the catheter to cause said at least one ablation element to contact a chamber wall about the vasculature ostium;
- ablating a lesion pattern on said chamber wall to electrically isolate the vasculature ostium; and
- further comprising visually displaying points of contact made between the at least one ablation element and targeted tissue using a feature made of an LED pattern corresponding to said contact points of the ablation element on the target tissue, wherein the visual display has an adjustable sensitivity setting to show the levels of contact.

7. A method for ablating a heart wall comprising:
- positioning at least one ablation device into a heart chamber;
- deploying an inflatable balloon at an orifice within the cardiac myocardium in which the balloon can be anchored;
- radially deploying at least one pre-shaped ablation element;
- ablating the heart wall with the at least one ablation element to create a lesion; and
- visually displaying points of contact made between the at least one ablation element and the heart wall;
- wherein the step of visually displaying comprises generating a light emitting diode (LED) pattern corresponding to points of contact made between the at least one ablation element and the heart wall.

8. A method for ablating a heart wall comprising:
- positioning at least one ablation device into a heart chamber;
- deploying an inflatable balloon at an orifice within the cardiac myocardium in which the balloon can be anchored;
- radially deploying at least one pre-shaped ablation element;
- ablating the heart wall with the at least one ablation element to create a lesion; and
- visually displaying points of contact made between the at least one ablation element and the heart wall;
- wherein the step of visually displaying comprises adjusting a sensitivity setting to show the level of contact made between the at least one ablation element and the heart wall.

* * * * *